United States Patent
Russie

(10) Patent No.: US 7,877,145 B2
(45) Date of Patent: Jan. 25, 2011

(54) SYSTEMS AND METHODS FOR MANAGING THE LONGEVITY OF AN IMPLANTABLE MEDICAL DEVICE BATTERY

(75) Inventor: Renold J. Russie, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 988 days.

(21) Appl. No.: 11/684,820

(22) Filed: Mar. 12, 2007

(65) Prior Publication Data

US 2007/0179549 A1    Aug. 2, 2007

Related U.S. Application Data

(62) Division of application No. 10/915,903, filed on Aug. 10, 2004, now Pat. No. 7,620,452.

(51) Int. Cl.
*A61N 1/00* (2006.01)
(52) U.S. Cl. ......................................................... 607/31
(58) Field of Classification Search ................... 607/27, 607/29, 30, 31, 59
See application file for complete search history.

(56) References Cited

U.S. PATENT DOCUMENTS

| | | | |
|---|---|---|---|
| 5,391,193 A * | 2/1995 | Thompson | 607/29 |
| 5,507,786 A * | 4/1996 | Morgan et al. | 607/27 |
| 6,671,552 B2 | 12/2003 | Merritt et al. | |
| 6,804,557 B1 | 10/2004 | Kroll | |
| 7,123,964 B2 | 10/2006 | Betzold et al. | |
| 2003/0114897 A1 | 6/2003 | Von Arx et al. | |
| 2003/0114898 A1 | 6/2003 | Von Arx et al. | |
| 2003/0130708 A1 | 7/2003 | Von Arx et al. | |
| 2003/0149459 A1 | 8/2003 | Von Arx et al. | |
| 2004/0039424 A1 | 2/2004 | Merritt et al. | |

\* cited by examiner

*Primary Examiner*—George Manuel
(74) *Attorney, Agent, or Firm*—Faegre & Benson LLP

(57) ABSTRACT

A method for managing battery longevity of an implantable medical device ("IMD") battery includes calculating a total IMD battery longevity value for an IMD and determining whether the total IMD battery longevity is below an optimal battery longevity value. At least one IMD parameter to be modified to improve the total IMD battery longevity value is automatically identified. The at least one automatically identified IMD parameter is adjusted to improve the total IMD battery longevity. Additionally, the improved total IMD battery longevity is displayed.

20 Claims, 6 Drawing Sheets

SYSTEMS AND METHODS FOR MANAGING THE LONGEVITY OF AN IMPLANTABLE MEDICAL DEVICE BATTERY

This application is a divisional of presently pending U.S. patent application Ser. No. 10/915,903, filed on Aug. 10, 2004, titled SYSTEMS AND METHODS FOR MANAGING THE LONGEVITY OF AN IMPLANTABLE MEDICAL DEVICE BATTERY, the contents of which are incorporated herein by reference.

TECHNICAL FIELD

The present invention relates generally to systems and methods for monitoring, configuring and managing implantable medical devices, and more particularly, to systems and methods for monitoring and managing battery longevity of the implantable medical devices.

BACKGROUND OF THE INVENTION

Cardiac pacemakers, implantable cardioverter defibrillators ("ICDs"), and cardiac resynchronization therapy ("CRT") devices are all implantable medical devices ("IMDs"). Pacemakers are designed to emit pacing stimuli to one or more chambers of the heart to treat bradyarrhythmia. ICDs typically have pacemaker functions and also include high voltage output capability that can be used to treat potentially lethal tachyarrhythmias. CRT devices provide pacing therapy to synchronize the left and right ventricles as a treatment for heart failure. CRT devices may or may not have high voltage defibrillation capability (CRT-P or CRT-D).

These devices are battery powered and, once implanted, require regular follow-up by a physician or health care professional to assess proper system operation and continued remaining battery capacity. The follow-ups typically occur at regular intervals, for example, every six months. Modern IMDs can communicate with an external computing device in a bi-directional fashion. This external computing device, known as a "programmer," allows the physician or health care professional to retrieve various diagnostic data, review stored history about the patient and device operation, and change various parameters of the device. The programmer also can show information related to battery status.

Batteries for IMDs typically use lithium iodide (LiI), lithium silver vanadium pentoxide (SVO), or lithium carbon monoflouride (CFx) chemistries. Depending on the chemistry, battery depletion status can be assessed by the device by measuring battery voltage, the time required to charge internal capacitors, use of a coulomb charge counter, or some combination of these or other methods. Specific algorithms for determining battery status vary by manufacturer, chemistry, and individual device.

Overall longevity for IMDs is estimated during the product development cycle. Models of battery capacity, expected variations in circuit performance, and clinical use conditions are all taken into account in these models. From this modeling effort, longevity estimates are created for various assumed clinical use conditions. The Instructions for Use (IFU) that is included in the finished device packaging and labeling will contain these battery longevity estimates.

During the life of the device, the estimated battery longevity remaining may be determined from a simple calculation of the estimated total longevity minus the portion of life already consumed from the battery. Many IMDs currently marketed can make such calculations and display them to the user through a programmer.

The longevity of an IMD may vary widely depending upon clinical use conditions. The programmed amplitude of pacing pulses, for example, can affect CRT device longevity by a factor of two or more (i.e., half the typical lifetime), depending on the number of pacing pulses the CRT device emits. Many physicians and health care professionals are surprised at the impact these clinical use conditions and parameter settings have on device longevity and express displeasure when overall longevity varies significantly from typical values.

Thus, a need exists for systems and methods that can inform physicians or health care professionals of circumstances that are leading to sub-optimal (shorter than usual device longevity, and can allow the physicians or health care providers to understand (and perhaps modify) specific parameters that are causing the sub-optimal longevity.

SUMMARY

A method for managing battery longevity of an implantable medical device ("IMD") battery includes calculating a total IMD battery longevity value for an IMD and determining whether the total IMD battery longevity is below an optimal battery longevity value. At least one IMD parameter to be modified to improve the total IMD battery longevity value is automatically identified. The at least one automatically identified IMD parameter is adjusted to improve the total IMD battery longevity. Additionally, the improved total IMD battery longevity is displayed.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION

In one embodiment, the purpose of this invention not only is to inform physicians or health care professionals of the device longevity remaining, but also to specifically draw their attention to situations in which overall device longevity will be significantly shorter than for typical devices and to enable them to understand and/or modify specific parameters that are causing the sub-optimal longevity.

In some embodiments, the system (and/or methods) of the present invention can work in conjunction with existing algorithms for calculating and/or displaying remaining device battery longevity estimates. In accordance with these embodiments, the system can calculate the overall expected longevity for a device and notify a user, for example, via a programmer screen icon (or some other display feature), that the device longevity is sub-optimal. The system then allows the user to navigate to another screen in the programmer, which can display the current values of the various parameters that determine battery life. The algorithm determines which parameters are outside of normal use settings and indicates those to the user. The user then is allowed to enter changes to those values to determine what impact the changes would have to battery longevity. The user then is allowed to make the changes to the device, if appropriate. The result is that at follow-up visits, the physician or health care professional is notified of conditions that will lead to sub-optimal device battery longevity and can be given an opportunity to make changes that will improve longevity.

Figure 1:
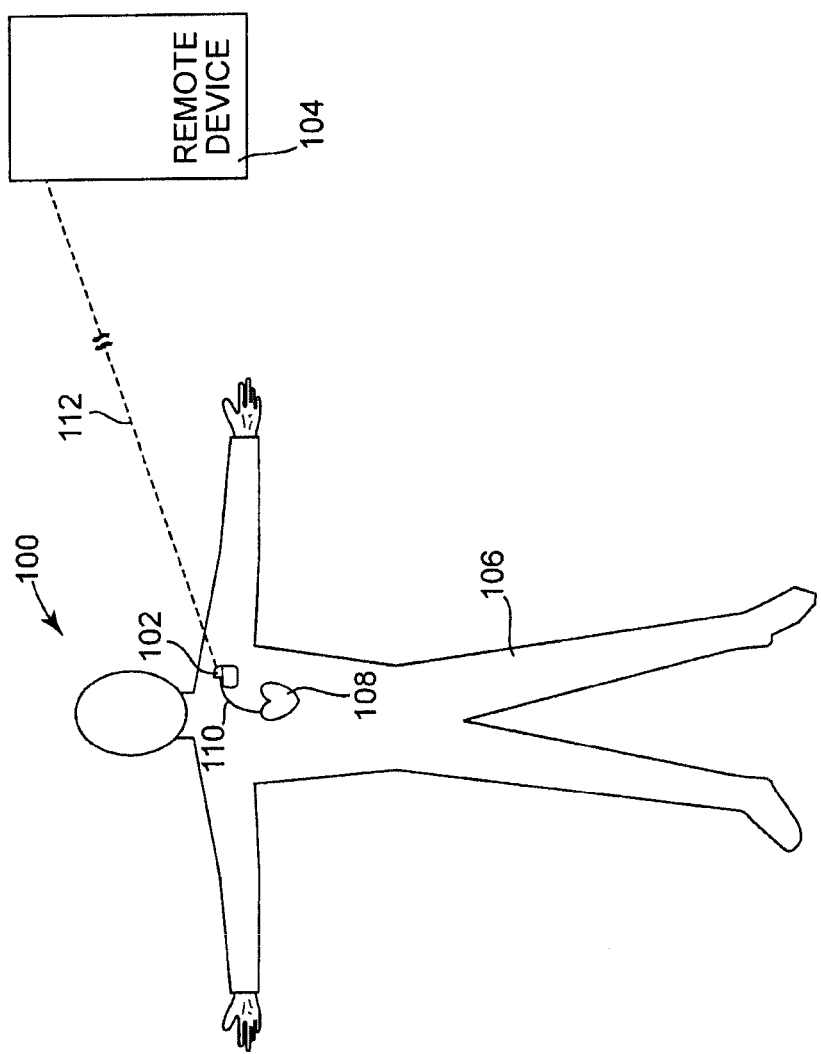
FIG. 1 is a schematic drawing showing one embodiment of a system, including an implantable medical device ("IMD"), that can be used to monitor and manage battery longevity for an IMD battery.

Referring now to FIG. 1, one embodiment of a system 100 for monitoring and managing battery longevity of an implantable medical device is shown. In accordance with the illustrated embodiment, system 100 includes an implantable medical device ("IMD") 102 and an external programming device 104. IMD 102 and external programming device 104 can communicate via a wireless communication link 112.

IMD 102 can be any type of implantable medical device that includes a battery. For example, IMD 102 can be cardiac rhythm management device ("CRM"), a ventricular assist blood pump, a drug delivery pump, a drug infusion device, a neurostimulating device, or any other suitable implantable device that includes a battery. In the embodiment illustrated in FIG. 1, IMD 102 is a CRM device, which is implanted within a patient's body 106 and coupled to the patient's heart 108 by a lead system 110. Examples of implanted CRM devices 102 include (but are not limited to) pacemakers, cardiac resynchronization ("CRT") devices, implantable cardioverter/defibrillators ("ICDs"), pacer/defibrillators, and the like.

Figure 2:
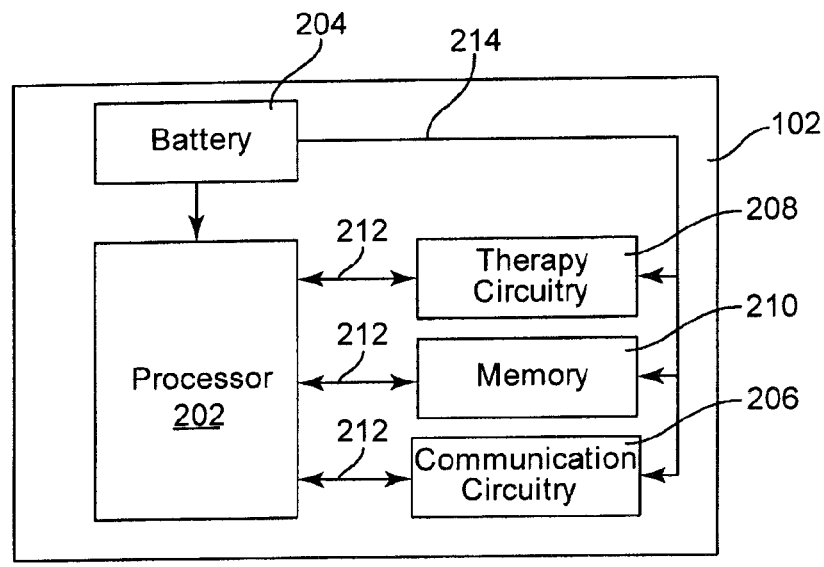
FIG. 2 is a block diagram showing some components of one embodiment of an IMD that can be used in the present invention.

Referring now to FIG. 2, one embodiment of an IMD 102 is illustrated. In accordance with the illustrated embodiment, IMD 102 comprises a processor 202, a battery 204, communication circuitry 206, therapy circuitry 208, and a memory 210. Communication circuitry 206, therapy circuitry 208 and memory 210 all are in electrical communication with processor 202, as is illustrated by arrows 212. In addition, battery 204 is configured to provide power to some or all the power consuming components within IMD 102. In the illustrated embodiment, for example, battery 204 provides power to communication circuitry 206, therapy circuitry 208 and memory 210 via electrical connection 214. In addition, as illustrated, processor 202 can receive power, as well as other battery parameters, such as current drain, depth of discharge, etc., from battery 204 via connection 216. As discussed in more detail below, the battery parameters can be used to determine battery longevity and other battery statistics.

As one skilled in the art will appreciate, processors and memory devices are well known in the art, and the specific type and/or style of processor or memory device that can be used in IMD 102 is not limited. Accordingly, processor 202 can be any suitable processing device currently known or hereinafter developed, and memory device 210 can be any suitable memory device currently known or hereinafter developed.

Communication circuitry 206 is circuitry that allows IMD 102 to communicate with other devices, such as external programming device 104, other IMDs, or other external devices. As discussed above, IMD 102 communicates with other devices via a wireless connection; e.g., wireless communication link 112. The wireless connection can be, for example, a near-field radio frequency (RF) communication connection, a far-field RF communication connection, an acoustical communication connection, an optical communication connection, or any other suitable wireless communication connection.

In one embodiment, communication circuitry 206 can include circuitry for both near-field RF telemetry and far-field RF telemetry. For example, one embodiment of communication circuitry that can be used in IMD 102 is disclosed in Published U.S. Patent App. No. US 2003/0114897 A1, published on Jun. 19, 2003, and entitled "Implantable Medical Device with Two or More Telemetry Systems," and Published U.S. Patent App. No. U.S. 2003/0114898 A1, published on Jun. 19, 2003, and entitled "Telemetry Duty Cycle Management System for an Implantable Medical Device," both of which are incorporated by reference herein for all purposes.

In addition, in other embodiments, power saving wireless communication circuitry and methods can be used. For example, the IMD communication circuitry 206 can be configured to reside in a power-saving, sleep mode for a majority of the time. In accordance with this embodiment, communication circuitry 206 can be configured to "wake-up" on a periodic basis to communicate with an external device. Upon "wake-up" the external device will monitor for RF activity, and if the external device locates it, communication between the IMD and the external device can be initiated. There are a number of different ways IMD power-saving modes can be implemented, and the present invention is not limited to any particular one. Indeed, the aforementioned Published U.S. Patent App. Nos. US 2003/0114897 A1 and US 2003/0114898 A1 disclose different ways of implementing IMD power-saving modes, which, as discussed above, are incorporated herein by reference for all purposes. In addition, alternative embodiments of power management systems and methods that can be used in the present invention are disclosed in Published U.S. Patent App. No. US 2003/0149459 A1, published on Aug. 7, 2003, and entitled "Methods and Apparatuses for Implantable Medical Device Telemetry Power Management," the entirety of which is incorporated by reference herein for all purposes.

Further, in accordance with other embodiments, communication circuitry 206 can be configured to communicate with an intermediary telemetry device, which, in turn, can facilitate communication with external programming device 104. One example of this type of configuration is disclosed in Published U.S. Patent App. No. US 2003/0130708, published on Jul. 10, 2003, and entitled "Two-Hop Telemetry Interface for Medical Device," the entirety of which is incorporated by reference herein for all purposes. Further, other configurations for RF telemetry are known, and communication circuitry 206 can embody those configurations, as well. Thus, as one skilled in the art will appreciate, communication circuitry 206 is not limited by any particular configuration or communication means.

Therapy circuitry 208 comprises circuitry for providing one or more therapeutic functions to a patient. For example, therapy circuitry 208 can include circuitry for providing heart pacing therapy, cardiac defibrillation therapy, and/or cardiac resynchronization therapy, drug delivery therapy, or any other therapy associated with a suitable IMD. In the case of cardiac therapy (e.g., pacing, defibrillation, etc.), therapy circuitry 208 includes cardiac leads 110 for delivering the therapy to particular locations in the heart.

In the embodiment illustrated in FIG. 1, external programming device 104 provides a user interface for system 100. The user interface allows a physician or other healthcare provider or caregiver to interact with IMD 102 through a wireless communication link 112. Wireless communication link 112 provides for bi-directional data communication between implanted CRM device 102 and external programming device 104, and as discussed above, can comprise any suitable wireless communication link 112, such as, a near-field RF communication connection, a far-field RF communication connection, an acoustical communication connection, an optical communication connection, or any other suitable wireless communication connection.

In one embodiment, RF telemetry link 112 provides for data transmission from IMD 102 to external programming device 104. This may include, for example, transmitting real-time physiological data acquired by IMD 102, extracting physiological data acquired by and stored in IMD 102, extracting therapy history data stored in IMD 102, and extracting data indicating an operational status of IDM 102 (e.g., lead impedance, battery status, battery longevity information, etc.). In addition, wireless communication link 112 can transmit data from external programming device 104 to IMD 102. This may include, for example, programming IMD 102 to acquire physiological data, programming IMD 102 to perform at least one self-diagnostic test (such as for a device operational status), programming IMD 102 to deliver at least one therapy, or changing one or more therapy parameter for the IMD.

Figure 3:
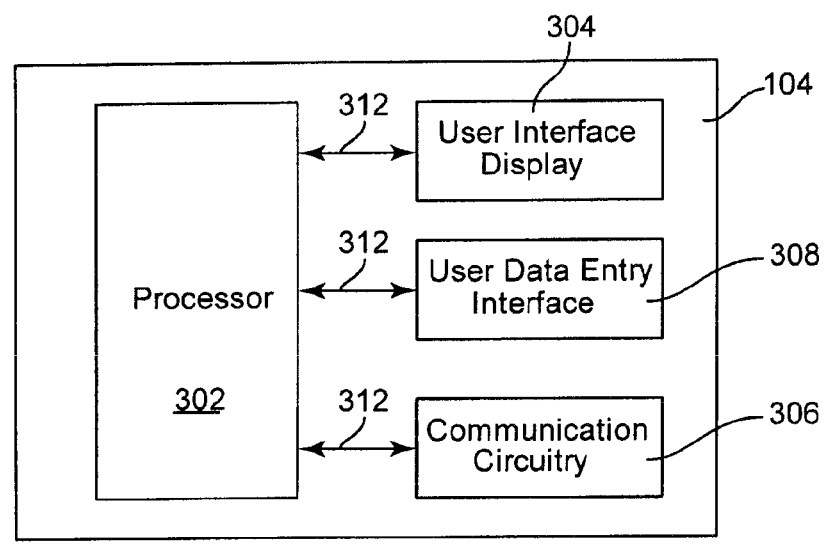
FIG. 3 is a block diagram showing some components of one embodiment of an external programming device that can be used with the present invention.

Referring now to FIG. 3, one embodiment of an external programming device 104 is shown. In the illustrated embodiment, external programming device 104 comprises a processor 302 (and associated memory (not shown)), a user interface display 304, communication circuitry 306 and a user date entry interface 308. User interface display 304, communication circuitry 306, and patient interface 308 all are in electrical communication with processor 302, as is illustrated by arrows 312.

As one skilled in the art will appreciate, and as discussed above with reference to IMD 102, processors and memory devices are well known in the art, and the specific type and/or style of processor or memory devices that can be used in external programming device 104 are not limited. Accordingly, processor 302 can be any suitable processing device currently known or hereinafter developed. Similarly, the memory (not shown) can be any suitable memory device currently known or hereinafter developed.

In addition, communication circuitry 306 is circuitry that allows external programming device 104 to communicate with IMD 102, and perhaps other devices. Thus, if IMD 102 is communicating via an RF connection, communication circuitry 306 comprises RF communication circuitry, as well. Similarly, if optical or acoustical communication connections are used, communication circuitry 306 is adapted to facilitate such connections. Thus, communication circuitry 306 can be any circuitry adapted to facilitate the wireless communications with IMD 102. As one skilled in the art will appreciate, such circuitry is known in the art, and therefore, will not be discussed in detail herein.

In the embodiment illustrated in FIG. 3, external programming device 104 includes a user interface display 304 and a user data entry interface 308, both of which facilitate communication with a user, such as a physician, or other health care provider or caregiver. For example, user interface display 304 is adapted to visually display or otherwise communicate various different IMD parameters and information for a user to view, and can be an electronic graphical user interface, a print-out display, or any other suitable interface display. Such interfaces are well known in the art, and thus, the present invention is not limited to any particular interface display. Examples of a few visual screens that may be displayed by user interface display 304 are shown in FIGS. 6-9, and are discussed in more detail below.

Similarly, user data entry interface 308 is an interface that allows a user to enter data and/or adjust IMD parameter values. Data entry interface 308 can be a keyboard device, a mouse, a touch screen, voice recognition technology, or any other suitable data entry interface. Again, data entry interfaces are well known in the art, and thus, the present invention is not limited to any particular data entry device or technology.

Figure 4:
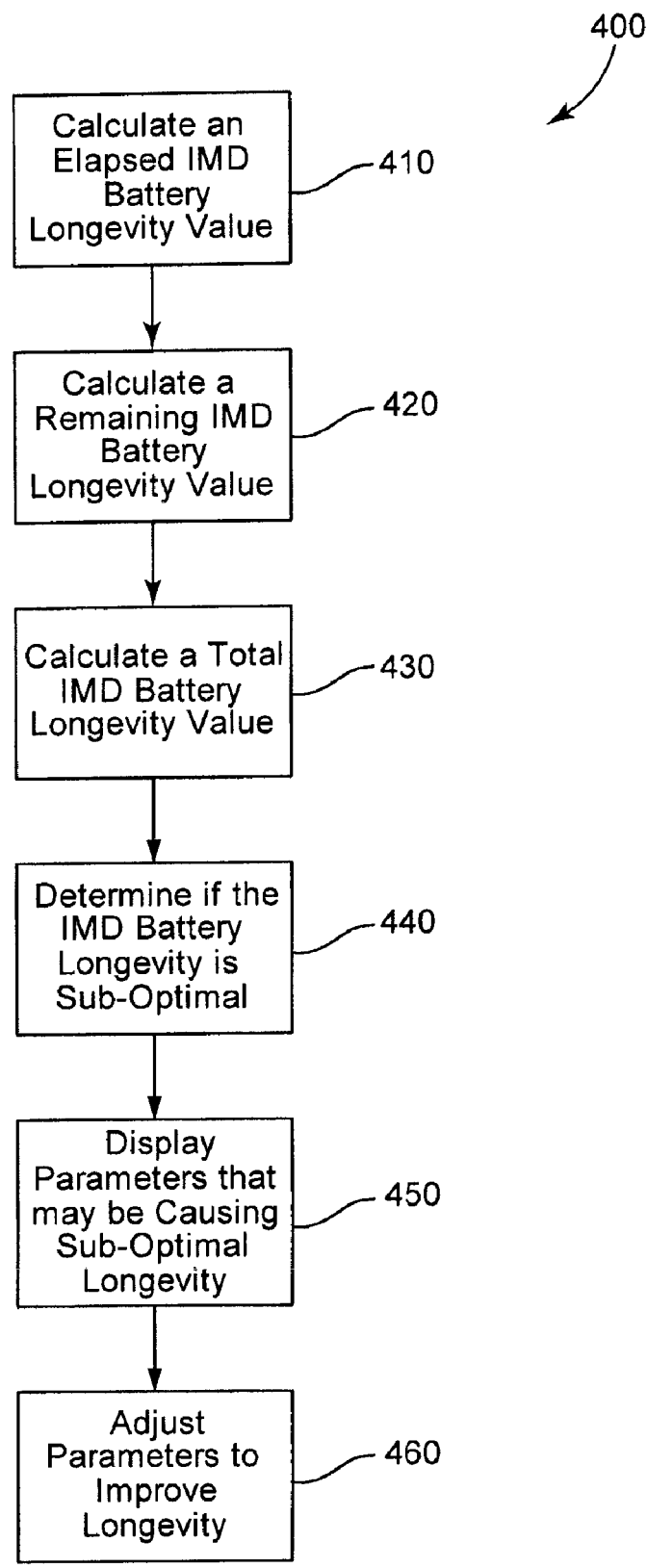
FIG. 4 is a flow chart illustrating one embodiment of a method for monitoring and managing battery longevity of an IMD battery.

Referring now to FIG. 4, one embodiment of a method for monitoring and/or managing battery longevity for an IMD battery is illustrated by flow chart 400. In accordance with the illustrated embodiment, the method comprises the steps of: (1) calculating an elapsed IMD battery longevity value (block 410); (2) calculating a remaining IMD battery longevity value (block 420); (3) calculating a total IMD battery longevity value from the elapsed value and the remaining value (block 430); (4) determining if the IMD battery longevity value is sub-optimal (block 440); (5) displaying and/or analyzing IMD parameters or settings that may be causing the sub-optimal longevity (block 450); and (6) adjusting parameters to perhaps improve the IMD battery longevity (block 460).

As one skilled in the art will appreciate, calculating an elapsed IMD battery longevity value is relatively straight forward, and in one embodiment, it merely is the elapsed battery life of the device since it was implanted in a patient. Also, there are a number of different methods and algorithms that can be used to calculate or determine a remaining battery longevity value; some of which are device and/or battery type dependent. Thus, any device longevity calculation algorithm or method can be used within the scope of the present invention.

Figure 5:
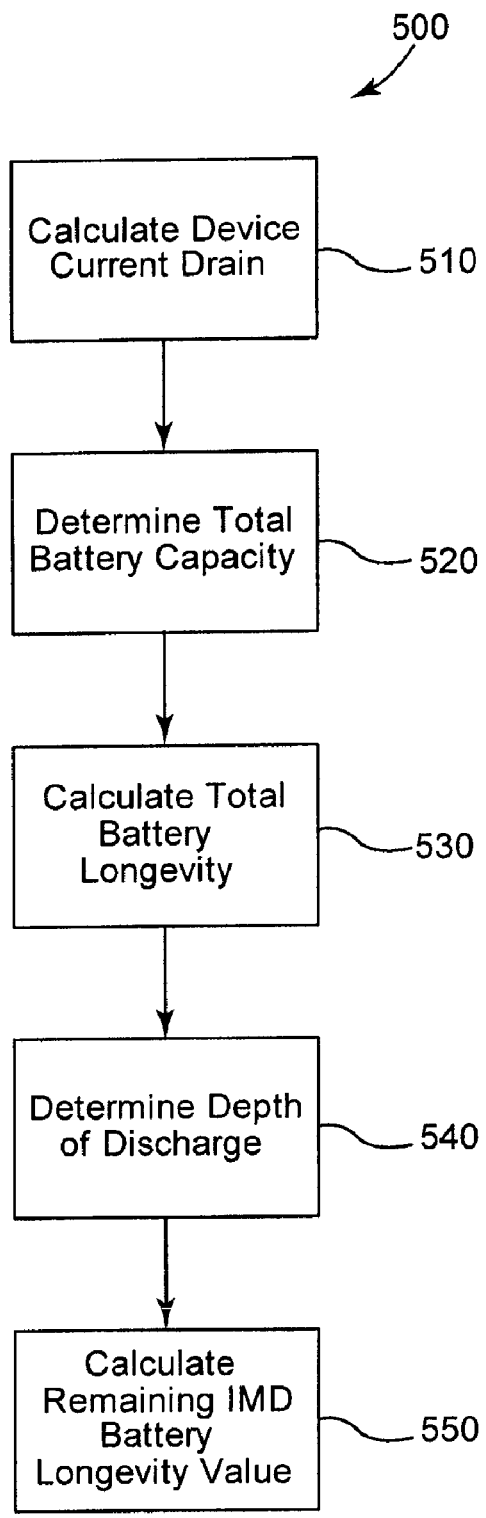
FIG. 5 is a flow chart illustrating one embodiment for calculating a remaining IMD battery longevity value.
Figure 6:
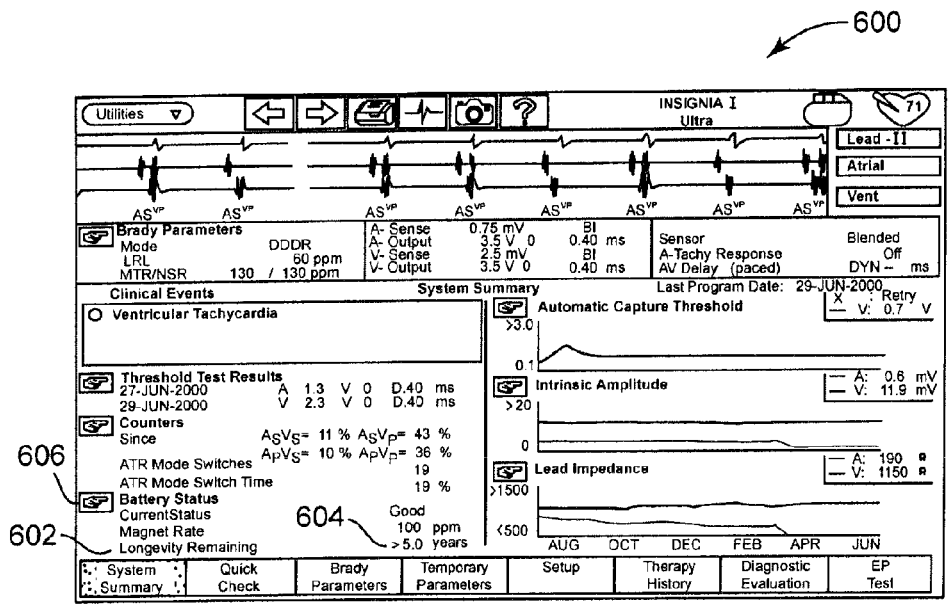
FIG. 6 is a screen shot of one embodiment of a user interface display screen that can be used to display battery longevity information to a user.

Referring to FIG. 5, one embodiment of a method that can be used to calculate a remaining IMD battery longevity value (block 420) for a CRM device, such as a pacemaker, is illustrated by flow chart 500. While the exemplary method illustrated in FIG. 5 will be described herein with reference to a pacemaker, one skilled in the art will appreciate that a similar method can be used to determine a remaining battery longevity value for other CRM devices and other IMDs, such as defibrillators, CRT devices, drug delivery devices, blood pumps, etc.

The first step of the method of FIG. 5 is to calculate a current drain for the IMD (e.g., pacemaker). In accordance with this particular embodiment, total pacemaker current drain at battery voltage can be calculated by:

$$I_d = I_q + I_a + I_v$$

where $I_d$ is the total pacemaker current drain, $I_q$ is the quiescent current drain of the pacemaker control circuitry (typically 7-10 μA depending on mode), $I_a$ is the Atrial pacing current, and $I_v$ is the ventricular pacing current.

Pacing current for a paced chamber can be calculated by:

$$I_{v/a} = \frac{P}{100} \times K_{\mathit{eff}} \times V_{set} \times C_{eq} \times \frac{LRL}{60}\left(1 - e\left(\frac{-PW}{Z \times C_{eq}}\right)\right) \times 10^6 \text{ (μA)}$$

where $I_{v/a}$ is the pacing current for the appropriate atrial or ventricular chamber in μA, P is the percent paced, $K_{\mathit{eff}}$ is an effective voltage multiplier setting (2.0 for pacing output of 3.5 volts), $V_{set}$ is the output voltage in volts, $C_{eq}$ is the equivalent pacing output capacitance formed by the series combination of the pacing supply capacitor and the output blocking capacitor (typically 2 μF) in Farads, LRL is the programmed lower rate limit (pacing rate) in pulses per minute (ppm), PW is the programmed pulse width in seconds, and Z is the pacing impedance in Ohms.

Thus, for example, pacing a chamber at 100%, 60 ppm, with a 0.4 ms pulse width, and a 3.5 V pacing output into a 500 ohm load requires approximately 4.6 μA of pacing current. Total current drain when both chambers are being paced at 100% is about 18 μA.

Next, in accordance with the method illustrated in FIG. 5, a total pacemaker battery capacity is determined (block 520). Total battery capacity Q typically is current drain dependent for a Lithium Iodide based pacemaker (i.e., $Q=f(I_d)$). Thus, as one skilled in the art will appreciate, overall capacity is lower at high current drain settings. A lookup table can provide the total battery capacity Q for the calculated current drain. A typical battery capacity at 20 μA current drain is about 1000 mAmp hours.

Next, an estimated battery longevity value L can be calculated as a function of current drain and total battery capacity as follows:

$$L = \frac{Q}{I_d} \times 10^3 \times \frac{1}{8760 \text{(hours/year)}}$$

where L is battery longevity in years, Q is total battery capacity in mAmp hours (e.g. 1000), and $I_d$ is current drain in μA.

Thus, for a battery with a 1000 mA-hr capacity and a current drain of 18 μA, the estimated battery longevity is about 6.3 years.

Next, depth of battery discharge is determined (block 540). As one skilled in the art will appreciate, internal battery measurements determine depth of discharge. While historically, this measurement has been a direct measurement of battery voltage, a more accurate measurement is the time required to charge the internal pacing supply capacitors. In one embodiment, depth of discharge is determined from this measurement under defined conditions using a lookup table. The output is a percent discharged.

Finally, the remaining battery longevity can be calculated as a function of the total longevity and the percent battery discharged (block 550), as follows:

$$T_{ERT} = L - (L \times D_\%)$$

where $D_\%$ is the percent battery discharged.

After the remaining battery longevity value has been calculated, it can be displayed to a user, for example, using external programming device 104. For example, as illustrated on screen 600 in FIG. 6, a battery longevity remaining value can be displayed on a screen for a user to view (see 602 and 604 in FIG. 6). For pacemakers that use lithium iodide batteries, accuracy of remaining longevity typically increases toward elective replacement time (ERT). Thus, in the illustrated embodiment, the display can indicate ">5.0 years" for calculations that indicate a longevity of greater than 5.0 years, and can show more accurate values as the time remaining gets smaller.

Figure 7:
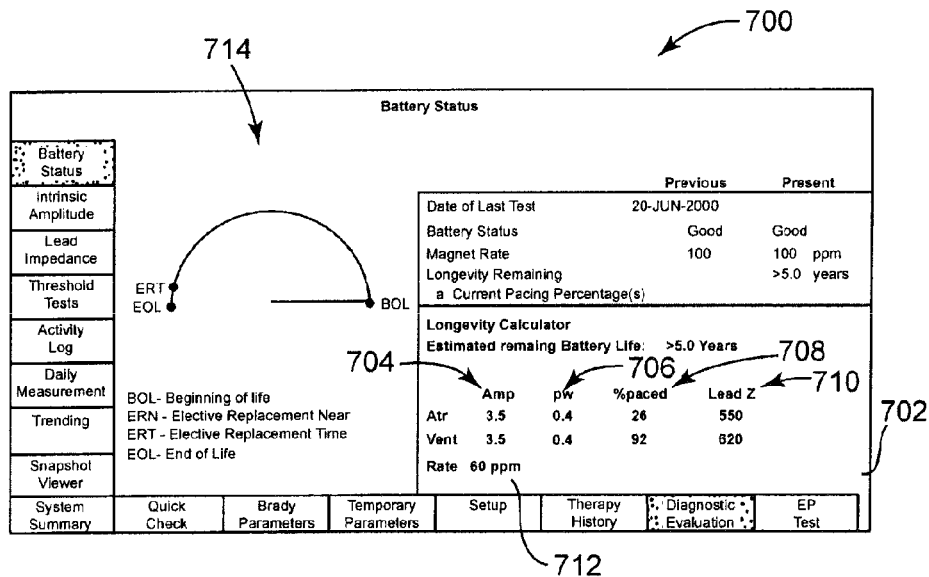
FIG. 7 is a screen shot of one embodiment of a user interface display screen that can display battery status information, including an interface for displaying and/or adjusting IMD parameters that may be affecting battery longevity.

In the illustrated embodiment, if a user wants additional information about battery longevity and perhaps IMD parameter settings that may affect the battery longevity, the user can select a battery icon, such as icon 606 on screen 600, to display more detail about battery status (see FIG. 7).

Referring to FIG. 7, user interface display screen 700 shows additional detail about battery status. In addition, screen 700 includes a longevity calculator 702 that can display (and modify) IMD parameters that may affect battery longevity. For example, in the illustrated embodiment, the relevant IMD parameters include pacing output amplitude 704, pulse width 706, percent paced 708, lead impedance 710 and pulse rate 712 for both the atrial and ventricle chambers. In addition, screen 700 can include a "gas gauge" display 714 showing battery life parameters, such as beginning of life (BOL), elective replacement near (ERN), elective replacement time (ERT), and end of life (EOL) parameters. When in this screen, a physician or clinician can modify the IMD parameters (e.g., parameters 704-712) on screen and analyze how remaining longevity would be impacted with the changes. This will be discussed in more detail below.

As mentioned above, once remaining battery longevity has been calculated, the system can determine if the overall or total battery longevity is sub-optimal (i.e., below the expected or average longevity). Overall or total battery longevity is the sum of the longevity already achieved by the device and the remaining longevity expected according to the calculations. Note that the longevity already achieved (also referred to as elapsed longevity) is a function of implant date and present date, both of which are available parameters in most IMDs. In accordance with one embodiment of the invention, external programming device 104 can analyze the overall or total battery longevity for IMD 102 and compare it to a nominal battery longevity value. In accordance with this embodiment, nominal longevity can be defined as the total battery longevity achieved when a pacemaker is paced 100% into both chambers at standard settings (e.g., pacing rate of 60 ppm, pacing output of 3.5 volts, and a pulse width of 0.4 ms) with a 500 ohm loads. In one embodiment, for example, the external programming device 104 can identify any IMD that will achieve a battery longevity of less than 80% of this nominal value.

Alternately, in accordance with another embodiment, the external programming device can identify any IMD that has an estimated total battery longevity that is less than a predetermined value. For example, in the case of a pacemaker, the predetermined value might be 4.0 years, or some other relevant value. Also, as one skilled in the art will appreciate, there may be other ways to classify a battery life as sub-optimal, which also can be used in the present invention. Thus, as one skilled in the art will appreciate, the present invention is not limited to any particular method for classifying a device longevity as sub-optimal.

Figure 8:
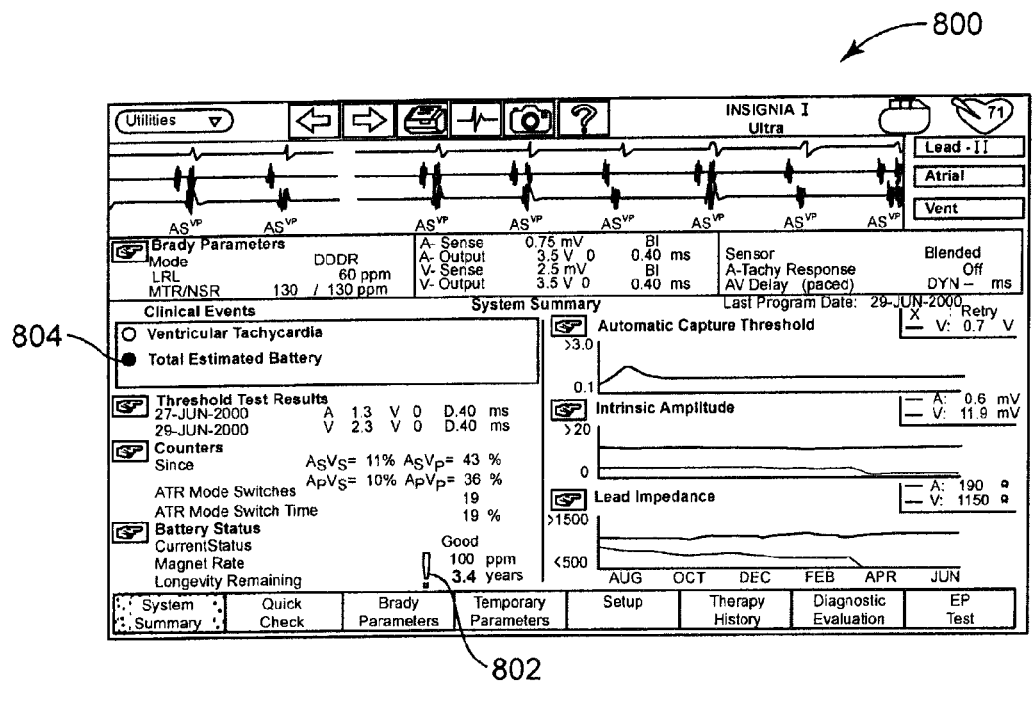
FIG. 8 is a screen shot of the user interface display screen of FIG. 6, but showing examples of how sub-optimal battery longevity warnings can be displayed.
Figure 9:
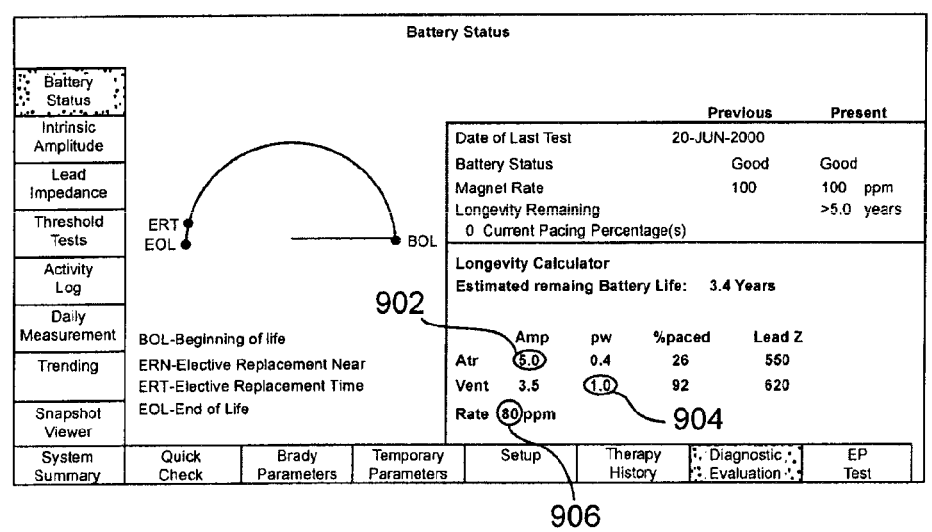
FIG. 9 is a screen shot of the user interface display screen of FIG. 7, but showing examples of how IMD parameters that may be affecting battery longevity can be displayed and/or highlighted.

If a device battery longevity is determined to be sub-optimal, a system summary screen, for example, screen 800 in FIG. 8, can display warning information for the user, such as displaying an exclamation mark 802 near the longevity remaining display and/or posting a battery longevity related clinical event 804 on the screen. Alternatively, other warning signals could be used, as well.

As a final step in the process, the external programming device can determine which IMD parameter settings, if any, are set to values that cause higher than normal current drain, thus resulting in a sub-optimal battery situation. For example, as illustrated on screen 900 of FIG. 9, parameters causing higher than normal current drain or parameters affecting the battery longevity can be highlighted. On screen 900, suspect parameters 902, 904 and 906 are circled. However, other highlights can be used, such as, red text, a bright background, etc. If IMD parameters have already been set back to nominal or lower values, no parameters will be highlighted on the screen.

By highlighting the suspect parameters, the physician and/or clinician can identify the parameters and use the longevity calculator or other user interface to determine how best to optimize or improve remaining battery longevity. That is, a physician can modify IMD parameter settings using the longevity calculator or other interface to determine how changing parameters will affect battery longevity. The physician can perform multiple combinations and permutations of parameter changes to test battery longevity improvements, while still providing proper therapy to the patient. Once the physician determines a proper setting for the IMD, the external programming device can communicate the new settings to the IMD, which, in turn, will implement the changes.

While the example set forth above has focused on a dual-chamber pacemaker, one skilled in the art will appreciate that the methods and systems described herein can be applied to other implantable medical devices as well, including implantable defibrillators and cardiac resynchronization devices. Thus, the present invention is not limited to any particular IMD configuration. In addition, while the embodiment discussed above describes the external programming device as performing the steps necessary to calculate the remaining device longevity value and total device longevity value, and to determine whether total battery longevity is sub-optimal, one skilled in the art will appreciate that in other embodiments, some or all of these functions could be performed within the IMD itself. In those embodiments, the external programming device would perform the functions that the IMD does not. In most cases, however, the external programming device will be used to display device longevity information to the user, and the external programming device will be used to adjust IMD parameters to optimize or improve battery longevity.

In conclusion, the present invention provides novel systems and methods for monitoring and managing battery longevity for IMD batteries. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method for managing battery longevity of an implantable medical device ("IMD"), comprising:
    calculating an elapsed battery longevity value for an IMD battery;
    calculating a remaining battery longevity value for the IMD battery;
    calculating a total IMD battery longevity value from the elapsed battery longevity value and the remaining battery longevity value;
    determining whether the total IMD battery longevity is sub-optimal;
    displaying at least one IMD parameter that affects the total IMD battery longevity; and
    adjusting the at least one IMD parameter to improve the remaining IMD battery longevity.

2. The method as recited in claim 1, further comprising:
    using the IMD battery to power a cardiac rhythm management device selected from the group consisting of a pacemaker, an implantable cardioverter defibrillator ("ICD"), a pacer/defibrillator, and a cardiac resynchronization ("CRT") device.

3. The method as recited in claim 1, wherein calculating a remaining battery longevity value for the IMD battery comprises:
    calculating an IMD current drain value;
    determining a total battery capacity value;
    calculating an estimated IMD battery longevity value from the total battery capacity and the IMD current drain value;
    determining a depth of discharge value; and
    calculating the remaining battery longevity value from the estimated battery longevity value and the depth of discharge value.

4. The method as recited in claim 1, wherein determining whether the total IMD battery longevity is sub-optimal comprises comparing the total IMD battery longevity value to a nominal longevity value.

5. The method as recited in claim 1, wherein determining whether the total IMD battery longevity is sub-optimal comprises determining if the total IMD longevity value is below a predetermined value.

6. The method as recited in claim 1, wherein an external programming device receives parameters from the IMD, and further wherein the external programming device calculates at least one of the elapsed battery longevity value, the remaining battery longevity value, and the total IMD battery longevity value.

7. The method as recited in claim 6, further comprising the external programming device displaying battery longevity information on a graphical user interface.

8. The method as recited in claim 1, wherein displaying IMD parameters that cause sub-optimal IMD battery longevity comprises an external programming device displaying the parameters on a graphical user interface.

9. The method as recited in claim 1, wherein adjusting the IMD parameters to improve the IMD battery longevity comprises adjusting the IMD parameters using an external programming device.

10. A method for managing battery longevity of an implantable medical device ("IMD") battery, the method comprising:
    calculating a total IMD battery longevity value for an IMD;
    determining whether the total IMD battery longevity is below an optimal battery longevity value;

automatically identifying at least one IMD parameter to be modified to improve the total IMD battery longevity value;

adjusting the at least one automatically identified IMD parameter to improve the total IMD battery longevity; and displaying the improved total IMD battery longevity.

11. The method as recited in claim 10, further comprising:
using the IMD battery to power a cardiac rhythm management device selected from the group consisting of a pacemaker, an implantable cardioverter defibrillator ("ICD"), a pacer/defibrillator, and a cardiac resynchronization ("CRT") device.

12. The method as recited in claim 10, wherein calculating the total IMD battery longevity value comprises:
calculating an elapsed battery longevity value for the IMD battery;
calculating a remaining battery longevity value for the IMD battery;
using the elapsed battery longevity value and the remaining battery longevity value to calculate the total IMD battery longevity value.

13. The method as recited in claim 12, wherein calculating the remaining battery longevity value for the IMD battery comprises:
calculating an IMD current drain value;
determining a total battery capacity value;
calculating an estimated IMD battery longevity value from the total battery capacity and the IMD current drain value;
determining a depth of discharge value; and
calculating the remaining battery longevity value from the estimated battery longevity value and the depth of discharge value.

14. The method as recited in claim 10, wherein determining from the total IMD battery longevity value whether the total IMD battery longevity is below the optimal battery longevity value comprises comparing the total IMD battery longevity value to a nominal longevity value.

15. The method as recited in claim 10, wherein determining from the total IMD battery longevity value whether the total IMD battery longevity is below the optimal battery longevity value comprises determining if the total IMD longevity value is below a predetermined value.

16. A method for managing battery longevity of an implantable medical device ("IMD") battery associated with an IMD, the method comprising:
calculating a total IMD battery longevity value using an external programming device programmed to communicate with the IMD, wherein the external programming device calculates an elapsed battery longevity value for the IMD battery, calculates a remaining battery longevity value for the IMD battery, and uses the elapsed battery longevity value and the remaining battery longevity to calculate the total IMD battery longevity value;
determining whether the total IMD battery longevity value is sub-optimal; and
identifying for modification at least one IMD parameter contributing to sub-optimal IMD battery longevity using the external programming device.

17. The method as recited in claim 16, further comprising:
providing a graphical user interface for selecting modified values for the displayed IMD parameters,
wherein the external programming device programs the IMD with the modified values to improve IMD battery longevity; and
displaying the improved IMD battery longevity.

18. The method as recited in claim 16, further comprising:
receiving parameters related to battery longevity from the IMD with the external programming device;
wherein the external programming device determines from the total IMD battery longevity value whether the IMD battery longevity is sub-optimal.

19. The method as recited in claim 16 further comprising:
highlighting the IMD parameters identified for modification on a graphical user interface.

20. The method as recited in claim 16, wherein determining whether the total IMD battery longevity value is sub-optimal comprises comparing the total IMD battery longevity value to a nominal longevity value.

* * * * *